United States Patent [19]

Hamasu

[11] 4,047,254
[45] Sept. 13, 1977

[54] MATTRESS CONSTRUCTION

[76] Inventor: Mituyoshi Hamasu, 31-13, 1-chome, Higashi Ikebukuro, Toshima, Tokyo, Japan

[21] Appl. No.: 674,910

[22] Filed: Apr. 8, 1976

[30] Foreign Application Priority Data

Dec. 13, 1975 Japan ................................ 50-149000

[51] Int. Cl.² .............................................. A47C 27/08
[52] U.S. Cl. ......................................... 5/345 R; 5/91; 5/284; 5/361 B
[58] Field of Search ...................... 5/91, 284, 354, 355, 5/345 R, 347, 361 B; 219/217, 528, 549; 128/24.5, 33, 362

[56] References Cited

U.S. PATENT DOCUMENTS

| | | | |
|---|---|---|---|
| 1,545,413 | 7/1925 | Elmvall | 128/24.5 |
| 1,948,067 | 2/1934 | Carreno et al. | 128/24.5 |
| 3,885,258 | 5/1975 | Reagan | 5/361 B |
| 3,924,284 | 12/1975 | Nelson | 5/284 |
| 3,974,532 | 8/1976 | Ecchuya | 5/91 |

Primary Examiner—Casmir A. Nunberg
Attorney, Agent, or Firm—McGlew and Tuttle

[57] ABSTRACT

A mattress construction comprises an intermediate layer of a semi rigid wave shaped resin material and with a top layer overlying the intermediate layer made of a resilient foamed resin material and a lower layer made of a resilient foamed resin material having a greater elastic restoring force than the upper layer. The greater elastic foamed restoring force may be accomplished by the increased density of the material being employed or by making the material of distinct substances giving the desired elastic characteristics. In one embodiment an electrified body in the form of a blanket is interposed between the intermediate layer and the top or upper layer.

4 Claims, 4 Drawing Figures

MATTRESS CONSTRUCTION

BACKGROUND OF THE INVENTION

1. Field of the Invention

This invention relates in general to the construction of mattresses and in particular to a new and useful mattress having intermediate semi rigid wave shaped portion and with upper and lower layers of different elastic characteristics on respective side of the intermediate portion.

2. Description of the Prior Art

Many types of mattress constructions are known and some of them are constructed for the purposes of affording the maximum comfort and still others are designed from the standpoint of the healthful support of the body. There are many concepts of what constitutes the proper support of the body both from the health standpoint and from a comfort standpoint.

SUMMARY OF THE INVENTION

The present invention is an improvement over the known constructions inasmuch as it provides a multi-layer mattress with a top layer which comes into direct contact with the body formed of a relatively soft material and constituting a soft layer with an intermediate layer formed as a relatively hard layer and a bottom layer designed to provide a thick but resilient support of the other layers. The bottom layer provides a general resilient backing for the upper two layers but holds the other two layers in a fixed relative position and the overall effect is a beneficial and healthful support for the body as well as a comfortable support.

In a preferred embodiment of the invention the intermediate semi rigid layer is wave shaped and advantageously includes wave shaped formations on both the tops and the bottom with the concave portions on one face being arranged beneath the convex portions on the opposite face. The upper layer advantageously is formed with a multiplicity of urethane foam particles having projections which engage into the concavities of the top face of the intermediate layer. The bottom layer is advantageously made more resilient than the upper layer so that the density of its particles are made greater than the particles of the upper layer.

Preferably the bottom face of the intermediate layer is made so that its convex areas are flattened off and its concave areas are made of a diameter which is smaller than the diameter of the opposite concave part of the top face. An electrified body in the form of a blanket is disposed on the top face of the intermediate layer and it may be energized to provide a body heating or electrifying device.

Accordingly it is an object of the invention to provide an improved mattress construction which includes an intermediate semi-rigid plastic material layer of wave shaped configuration in a top layer of a resilient plastic foam material and a bottom layer of a similar foam material having a greater elastic restoring force than the upper layer.

A further object of the invention is to provide a mattress which includes an intermediate semi-rigid layer between two resilient layers of varying resiliency and wherein the intermediate layer is provided with a wave shaped top face underlying a similarly reversely formed upper layer.

A further object of the invention is to provide a mattress which is simple in design, rugged in construction and ecnomical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawings and descriptive matter in which there are illustrated preferred embodiments of the invention.

BRIEF DESCRIPTION OF THE DRAWINGS

Shown in the drawings attached hereto are illustrations of the present invention.

DETAILED DESCRIPTION OF THE INVENTION

Figure 1:
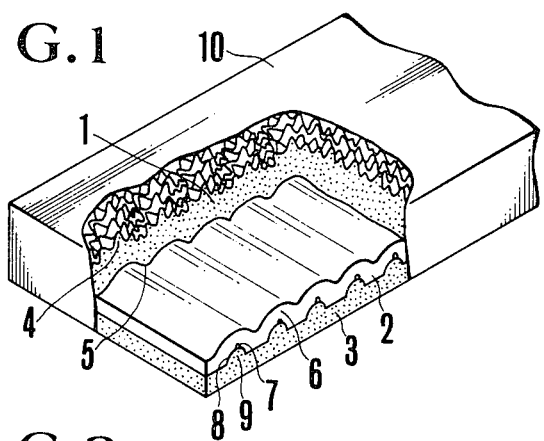
FIG. 1 is a partially cutaway perspective of a mattress of the triple layer construction system introduced in the present invention.

A detailed description of the present invention will be given below by making reference to an illustration thereof shown in the drawings.

Figure 2:
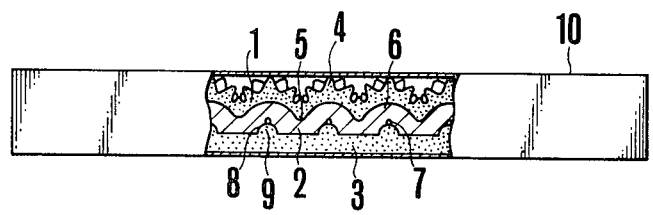
FIG. 2 is a partially cutaway view of the side of the mattress of the triple layer construction system shown in FIG. 1.

In FIG. 1 and FIG. 2, 1 represents the top layer, 2 represents the intermediate layer, 3 represents the bottom layer, and the said layers are respectively formed in such a manner as is set forth below.

The top layer 1 is made of such elastic foamed synthetic resin as has restoring force against compression, for instance, urethane foam of 0.016 in specific gravity, and the top surface thereof has a plurality of projections 4. Other suitable materials the top layer includes polyurethane foam, and elastic foamed synthetic resin having restoring force characteristics against compression. The intermediate layer 2 is made of semi-rigid foamed synthetic resin, for example, polyethylene foam, and the shape thereof is such that the top surface thereof has corrugation of concaves 5 and convexes 6 formed thereon, and the lower surface thereof has such concaves 8 having a radius larger than that of the concave 5 of the corrugation on the top surface.

The radius of the concave section 5 on the top surface of the intermediate layer 2 is 11R, that of the convex section on the said top surface is 37.5R, and that of the concave section on the lower surface is 19R, respectively. The said values of the respective radii represent typical ones, which may be subjected to modification to meet the requirement in a practical case. Other kinds of hard foamed synthetic resins eligible for selection include ABS resins, styrene foam, styrol foam, urethan rubber, and the like; furthermore, now that the only thing required of the hard foamed synthetic resin to be selected in this case is that a certain degree of hardness can be maintained against a load applied thereon, it goes without saying that any other hard foamed synthetic resin of this category can be employed for this purpose.

The bottom surface of the intermediate layer 2 has flattened convex portions between the concave portions 9.

The bottom layer 3 is made of an elastic foamed synthetic resin having a composition effecting a greater restoring force against compression than the top layer. The material of the bottom layer employed in this illustration is urethane foam of 0.02 in specific gravity.

Figure 3:
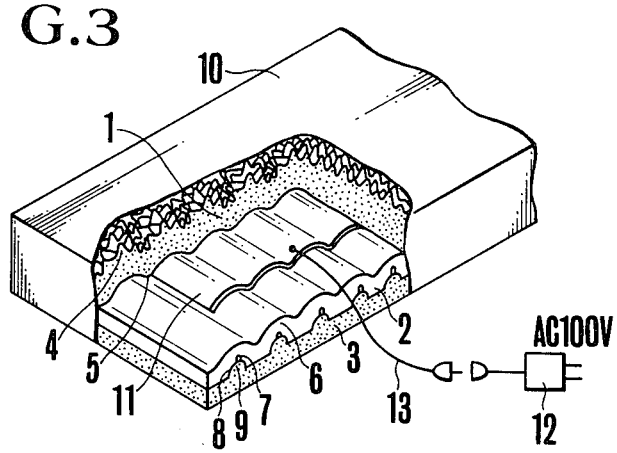
FIG. 3 is a partially cutaway perspective of another illustration of the mattress of the triple layer construction system shown in FIG. 1 to which potential therapeutics by high-load voltage is applied.
Figure 4:
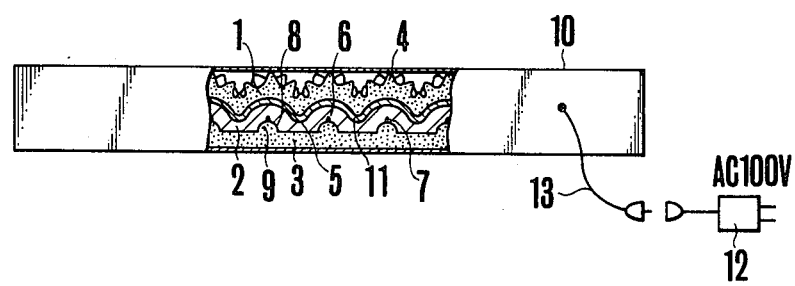
FIG. 4 is a partially cutaway view of the side of the mattress of the triple layer construction system shown in FIG. 3.

And, the top layer 1 and the intermediate layer 2 are incorporated into an integral entity in such a manner that the projections 4 formed on the surface of the top layer 1 are set in such a manner as to be projected above the top surface of the mattress. The lower surface of the top layer 1 is bonded to the top surface of the intermediate layer 2. The intermediate layer 2 and the bottom layer 3 are incorporated into an integral entity in such a manner that the convex sections 9 formed on the top surface of the bottom layer 3 and the concave sections 8 formed on the lower surface of the intermediate layer 2 are fitted and bonded with each other by the employment of a proper bonding agent. The three layers are wrapped with a cover 10. As shown in FIGS. 3 and 4, the top layer 1 is made of such elastic foamed synthetic resin having a restoring force against compression, and has a plurality of projections 4 formed on the upper surface thereof, the intermediate layer 2 is made of a hard foamed synthetic resin as has a certain degree of hardness and resistance to a load applied thereon, the top surface thereof has concaves 5 and convexes 6 of the corrugation properly formed thereon, the lower surface thereof has concave sections 8 of a radius larger than that of the concave sections 5 of the corrugation on the top surface properly formed at such positions on the lower surface as are corresponding to the convex sections 6 of the corrugation on the top surface, and the said concave sections 8 have a slit 7 properly formed therein by cutting-out, and the bottom layer 3 is made of such elatic foamed synthetic resin which has a greater restoring force than that of the elastic foamed synthetic resin constituting the top layer 1 and having restoring force, and has a number of convex sections 9 corresponding the concave sections 8 formed in the lower surface of the intermediate layer 2 properly formed on the top surface thereof.

The said respective layers formed in such a manner as is set forth above are properly laminated by the application of the same processes as those in the case of the illustration shown in FIG. 1 and FIG. 2; however, in the case of this illustration, an electrified body 11 is positioned on the top surface of the intermediate layer 2, and the top layer 1 is set in place over electrified body 11 and laminated thereto. The bottom layer and the intermediate layer are laminated in exactly the same manner as in the case of the illustration shown in FIG. 1 and FIG. 2. The said electrified body 11 is connected, by means of a conductor 13, to a high-voltage power source device 12 specifically designed for applying high-load voltage on the electrified body 11.

Now that the mattress introduced in the present invention is of such a type of construction as is set forth in the preceding paragraphs, the functions performed, and the effects achieved, by the mattress are generally as set forth below.

When a person lies on the mattress, the top layer 1 being made of such foamed synthetic resin as has sufficient elasticity to hold the person softly and gently. The bottom layer 3 having an elastic synthetis resin with a higher elasticity than that of the top layer wards off in a gentle manner the impact applied thereon, while holding flat the intermediate layer 2 made of hard foamed synthetic resin, until the whole impact is absorbed in a proper manner. Both are different specific gravities. Because the material of the bottom layer 3 has a higher specific gravity than the material of the top layer 1 absorption of the impact is conducted in such a sequence that the top layer 1 precedes the bottom layer 3. Such a system of construction as is set forth in details above, when combined with the intermediate layer 2 that is made of hard foamed synthetic resin serves to enable the body lying and held on the mattress to be kept in place, with a proper lying posture retained at all times. The design of intermediate layers with concave sections of a larger radius than concave sections 5 of the corrugation on the top surface and which are formed at positions on the lower surface of the intermediate layer 2 aligned with the convex sections 6 of the corrugation formed on the top surface thereof and with the slit 7 specifically added thereto provides the effect of a spring. Furthermore, repetitive arrangement of rather large concaves 5 and convexes 6 of the intermediate layer 2 induces achieving chiropractic effects on the body, and, in addition thereto, the thin projections 4 formed on the lower surface of the top layer 1 likewise serves for achieving the chiropractic effects in a delicate and comfortable manner.

Besides, in the case of the illustration shown in FIG. 3 and FIG. 4, when a high-voltage power source device such as a blanket 12 (which is connected with, for instance, a service line of AC 100V) is used with a conductor 13 properly connected therewith, the electrified body 11 has high-load voltage properly applied thereon, and the body is put in high electrostatic potential, thus enabling potential therapeutics to be conducted by virtue of an ionic effect.

What is claimed is:

1. A mattress construction comprising an intermediate layer of a semi-rigid resin material having top and bottom surfaces with continuous outwardly projecting wave formations adjacent inwardly projecting concavities with the concavities of the bottom surface having a larger radiuus of concavities than that of the top surface and being formed in vertical alignment below the wave-shaped formations of said top surface, a top layer overlying said intermediate layer made of a resilient foam resin material and having a resiliency so as to become restored to its original shape after unloading, said top surface having a multiplicity of projections formed thereon in a regular spaced-apart pattern with concavities between adjacent projections, and a lower layer of a foamed resin material having a greater elastic restoring force than said top located below said intermediate layer.

2. A mattress according to claim 1, including a slit defined in the tops of the concave portions on the bottom surface of said intermediate layer.

3. A mattress according to claim 1, including a blanket of material forming an electrical power device disposed on the top surface of said intermediate layer.

4. A mattress according to claim 1, wherein the density of said top layer is less than the density of said bottom layer, a cover enclosing said layers, said intermediate layer having concavities aligned with said projections of said top layer, said top layer being formed of a separate multiplicity of polyurethane portions and said upper and bottom layers being bonded to said intermediate layer.

* * * * *